United States Patent [19]

Nagasaki

[11] Patent Number: 4,780,762
[45] Date of Patent: Oct. 25, 1988

[54] IMAGE SIGNAL CORRECTING CIRCUIT
[75] Inventor: Tatsuo Nagasaki, Musashino, Japan
[73] Assignee: Olympus Optical Co., Ltd., Tokyo, Japan
[21] Appl. No.: 937,641
[22] Filed: Dec. 3, 1986
[30] Foreign Application Priority Data Dec. 4, 1985 [JP] Japan .................................. 60-272885
Dec. 27, 1985 [JP] Japan .................................. 60-295921

[51] Int. Cl.⁴ .............................................. H04N 5/14
[52] U.S. Cl. .................................... 358/166; 358/167; 358/98
[58] Field of Search ............... 358/166, 169, 168, 164, 358/98, 37, 32, 160, 163, 167

[56] References Cited
FOREIGN PATENT DOCUMENTS
61-62440 3/1986 Japan .

OTHER PUBLICATIONS
Riolfo, Benedetto, "Techniques for Two-Level Coding of T.V. Signals" CSELT Rapporti Technici, vol. VIII, No. 2, pp. 131-138, 1979.

Primary Examiner—John W. Shepperd
Assistant Examiner—David F. Harvey
Attorney, Agent, or Firm—Armstrong, Nikaido, Marmelstein & Kubovcik

[57] ABSTRACT

Picture quality is improved by reducing an influence such as an illumination unevenness caused on the low band side by providing an image signal correcting device comprising a logarithmic compressing device for logarithmically compressing an image signal, a two-dimensional filter device of a characteristic of suppressing the low band side and relatively enhancing the high band side of this logarithmically compressed image signal and an exponential converting device for converting the image signal having passed through this two-dimensional filter to be of an exponential characteristic.

7 Claims, 12 Drawing Sheets

FIG.8
(a) 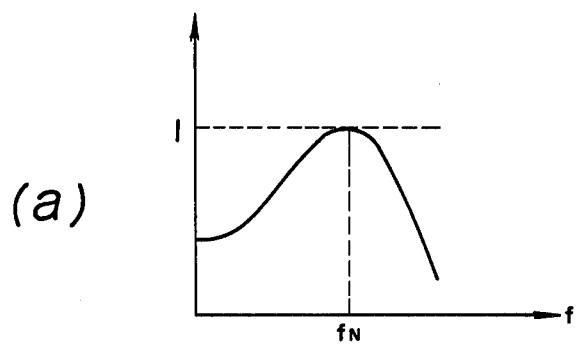
(b) 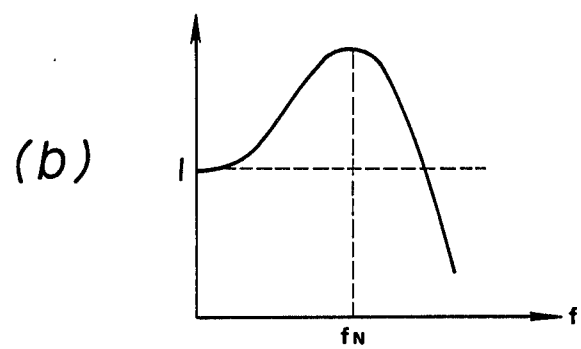
(c) 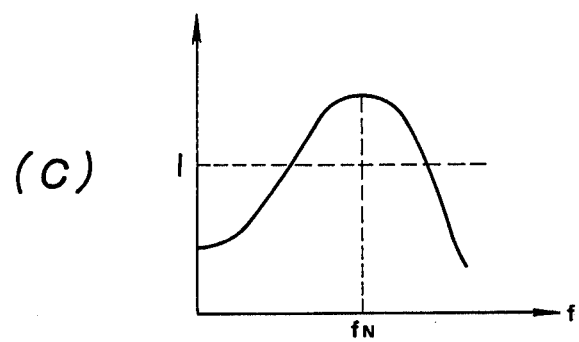

FIG. 14
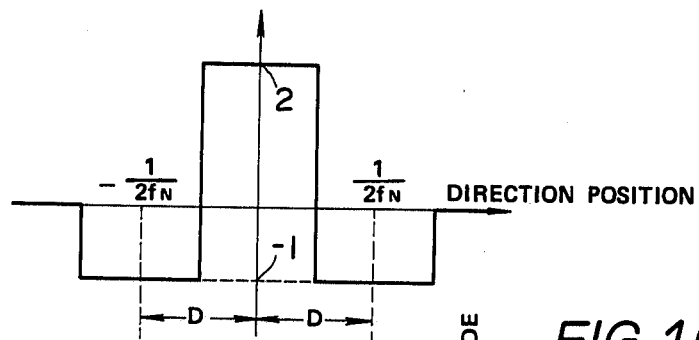
FIG. 15
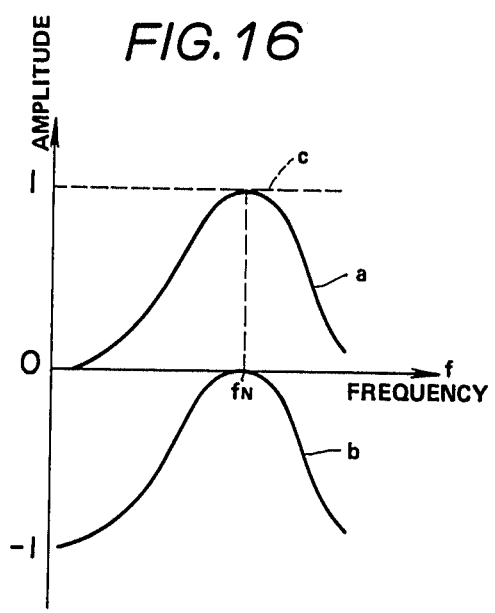
FIG. 16

IMAGE SIGNAL CORRECTING CIRCUIT

FIELD OF THE INVENTION AND RELATED ART STATEMENT

This invention relates to an image signal correcting circuit for processing images to suppress an illumination unevenness or the like for an endoscope or the like using a solid state image pickup element.

Recently, there is extensively used an endoscope whereby an affected part or the like within a body cavity can be diagnosed by inserting an elongated inserting part without requiring any incision or can be cured by inserting a treating instrument as required. In the above mentioned endoscope, an image of such an object part as an affected part is formed by an image forming lens arranged on the tip side of the inserting part. This formed image is transmitted to the hand side by such optical image transmitting means as a fiber bundle and can be magnified and observed with an eyepiece system.

Now, among encoscopes, an electronic endoscope (which shall be mentioned as an electronscope hereinafter) whereby an optical image is formed on an image pickup surface of a solid state image pickup element such as a CCD by an image forming lens without using the above mentioned optical image transmitting means and an electric image signal photoelectrically converted by this solid state image pickup element is displayed on a monitor pickup surface is so easy to record or reproduce images as to be extensively used hereafter.

However, even in the image by the above mentioned electronscope, in most cases, there are many tubularly hollow or very irregular objects in the state of using the electronscope and the fluctuation of the distance from the scope to the object to be imaged is 2 to 20 cm. within the same picture surface, showing a difference of about 10 times. The illumination is so close to the spot light source that the difference of the distance becomes a large illumination unevenness. That is to say, there occurs such phenomenon that a near object to be imaged causes a strong halation but a far object is dark and invisible. As a means of solving it, such automatic light adjusting system as is shown, for example, in Japanese Patent Application No. 183083/1984 (Laid Open No. 62240/1986) has been used in an electronscope.

However, the principle of the above mentioned conventional automatic light adjusting system is to keep the average value of the brightness of an image constant and does not basically improve the latitude. That is to say, a far dark part and a near bright part can not be simultaneously displayed with a proper brightness within the same picture surface.

OBJECTS AND SUMMARY OF THE INVENTION

The present invention is made in view of the above described points and has it as an object to provide an image signal correcting circuit adapted to an electronscope or the like whereby the influence of an illumination fluctuation or the like is reduced and an image easy to diagnose can be realized.

Another object of the present invention is to provide an image signal correcting circuit wherein the outline and structure by the enhancement on the high band side of an image signal can be enhanced and the noise in the part in which S/N is small can be controlled.

In the present invention, the picture quality is improved by reducing an influence such as of an illumination unevenness caused on the low band side by providing an image signal correcting device comprising a logarithmic compressing device for logarithmically compressing an image signal. A two-dimensional filter device has a characteristic of suppressing the low band side and relatively enhancing the high band side of this logarithmically compressed image signal. A exponential converting device converts the image signal having passed through this two-dimensional filter to be of an exponential characteristic.

Further, in the above mentioned image signal correcting means, a filter characteristic variable device is provided so that the gain on the high band side and the gain on the low band side in the two-dimensional filter device can be respectively independently variably set and not only the illumination unevenness can be eliminated but also the outline and structure can be effectively enhanced.

BRIEF DESCRIPTION OF THE DRAWINGS

FIGS. 1 to 9 relate to the first embodiment of the present invention.

FIG. 1 is a formation view showing an electronscope provided with the first embodiment.

FIG. 2 is a block diagram showing the formation of a logarithmic filter circuit as an image signal correcting circuit of the first embodiment.

FIG. 3 is an explanatory diagram for explaining the manner of forming the logarithmic characteristic of a logarithmic amplifier.

FIG. 4 is a characteristic diagram showing the spatial frequency characteristic of the filter in the case of one dimension.

FIG. 5 is a pulse waveform view for a pulse responding process to realize the characteristic of FIG. 4.

FIG. 6 is an explanatory view showing a coefficient distribution in a two-dimensional filter to obtain the filter characteristic shown by FIG. 4.

FIG. 7 is a circuit diagram showing a concrete circuit formation of the two-dimensional filter.

FIG. 8a-c shows characteristic diagrams showing that the filter characteristic varies with the value of a parameter.

FIG. 9 is an explanatory diagram showing the manner of forming the exponential characteristic of an exponential amplifier.

FIGS. 12 to 18 relate to the second embodiment of the present invention.

FIG. 12 is a formation view showing an electronscope provided with the second embodiment.

FIG. 13 is a block diagram showing a formation example of the logarithmic filter circuit of the second embodiment.

FIG. 14 is an explanatory view showing a picture element arrangement in the case of filtering.

FIG. 15 is a waveform diagram in the case of an impulse responding process in respective directions.

FIG. 16 is a filter characteristic view realized by the impulse response of the waveform of FIG. 15.

FIG. 17 is an input-output characteristic diagram of a noise suppressing circuit.

FIG. 18 is a characteristic diagram showing the filter characteristic realized by the second embodiment.

DETAILED DESCRIPTION OF PREFERRED EMBODIMENTS

Figure 1:
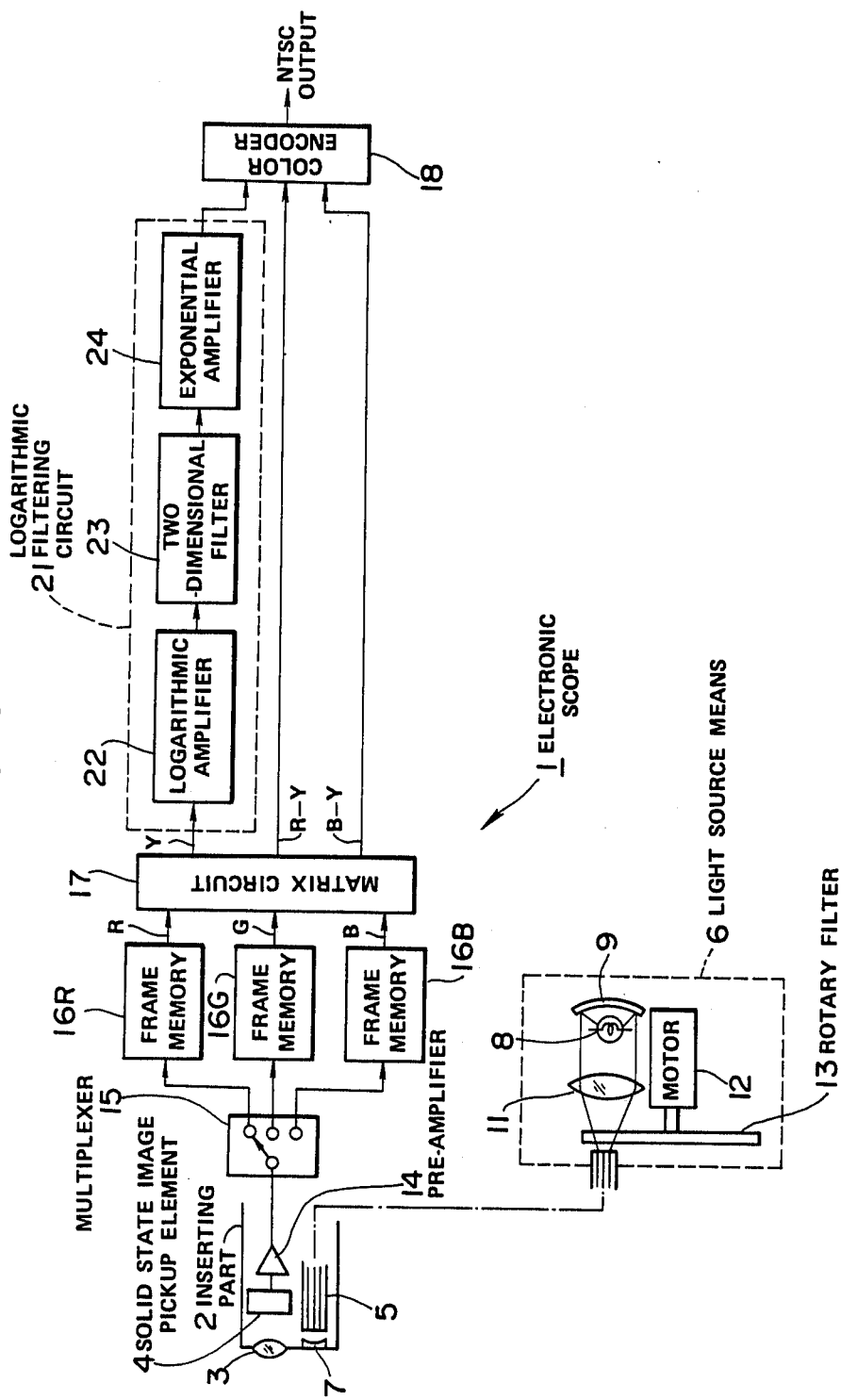

As shown in FIG. 1, in an electronscope provided with the first embodiment, an image forming lens 3 is arranged on the tip side of an elongated inserting part 2 so as to be able to be inserted into a body cavity or the like and a solid state image pickup element 4 such as a CCD is arranged on the focus plane of the image forming lens 3 to form an image pickup means. A light guiding fiber 5 is inserted through the above mentioned inserting part 2 so that an illuminating light of an external light source device 6 can be transmitted and projected onto the object side through a light distributing lens 7 from the tip surface.

In the above mentioned light source device 6, the illuminating light of a light source lamp 8 is reflected by a concave mirror 9 and this reflected light is collected and projected onto the entrance end of a light guiding cable connected to the light guiding fiber 5. In case it is collected and projected, when it is passed through a rotary filter 13 which is provided with filters passing respectively three primary colors and provided around the rotary shaft and which is rotated and driven by a motor 12, it will be projected as illuminating lights of the respective wavelengths of the three primary colors. Therefore, the object to be imaged will be illuminated in turn with the illuminating lights of the respective three primary colors.

Now, the image signal of the optical image photoelectrically converted by the above mentioned solid state image pickup element 4 is amplified by a preamplifier 14 of a low noise exponent, is passed through an A/D converter not illustrated and is then recorded in turn by one frame under the illuminations of the respective colors through a multiplexer 15 on the hand side into a frame memory 16R for red, frame memory 16G for green and frame memory 16B for blue. The signals recorded in these frame memories 16R, 16G and 16B are passed through a D/A converter not illustrated and are then simultaneously read out and a brightness signal Y and two color difference signals R-Y and B-Y are taken out through a matrix circuit 17.

The above mentioned two color difference signals R-Y and B-Y are put into a color encoder 18. On the other hand, the brightness signal Y is put into the above mentioned color encoder 18 through a logarithmic filtering circuit 21 forming the image signal correcting circuit of the first embodiment. A color image (video image) signal of an NTSC system is put out of this color encoder circuit 18. This color video signal is put into a color monitor not illustrated and a color picture image is displayed on a color picture surface.

The above mentioned logarithmic amplifier 21 is formed of a logarithmic amplifier 22 logarithmically compressing the input brightness signal Y, a two-dimensional filter 23 showing a high pass filter characteristic of suppressing the low band side and passing the high band side relatively to this logarithmically compressed brightness signal and an exponential (reverse logarithmic) amplifier 24 putting in the signal having passed through this two-dimensional filter 23 to make it an output of an exponential function.

The above mentioned logarithmic filtering circuit 21 performs substantially as follows:

When an illumination unevenness is produced depending on the distance (that is, the distance difference) from the exit end of the illuminating light to an object to be imaged of coordinates (x, y), the illumination unevenness intensity distribution is represented by F(x, y) and the reflex intensity is represented by G(x, y), the optical image Y(x, y) formed on the image pickup surface of the solid state image pickup element 4 will be represented by $$Y(x,y) = F(x,y) \cdot G(x,y)$$

The coordinates of the above mentioned optical image Y(x, y) is changed to time coordinates (x',y') on the displayed picture surface in the monitor but the brightness distribution on the displayed picture surface holds substantially the above mentioned relation.

Therefore, the brightness output log Y(x', y') logarithmically compressed by the logarithmic amplifier 23 will be $$\log Y(x',y') = \log F(x',y') + \log G(x'y').$$

As the intensity distribution by the above mentioned illumination unevenness is usually of a low frequency, by passing it through the two-dimensional filter 23 passing the high band side, the element log F(x',y') by the illumination unevenness can be substantially eliminated and only log G(x',y') can be taken out. By further passing this signal through the exponential amplifier 24, a brightness signal represented by G(x'y') can be obtained. The color video signal of the NTSC system put out of the color encoder circuit 18 becomes a signal with which the influence of the illumination unevenness is reduced and the far part does not become too dark and which is represented as a picture image easy to diagnose.

The first embodiment shall be explained in detail in the following with reference to FIG. 2 and others following it.

Figure 2:
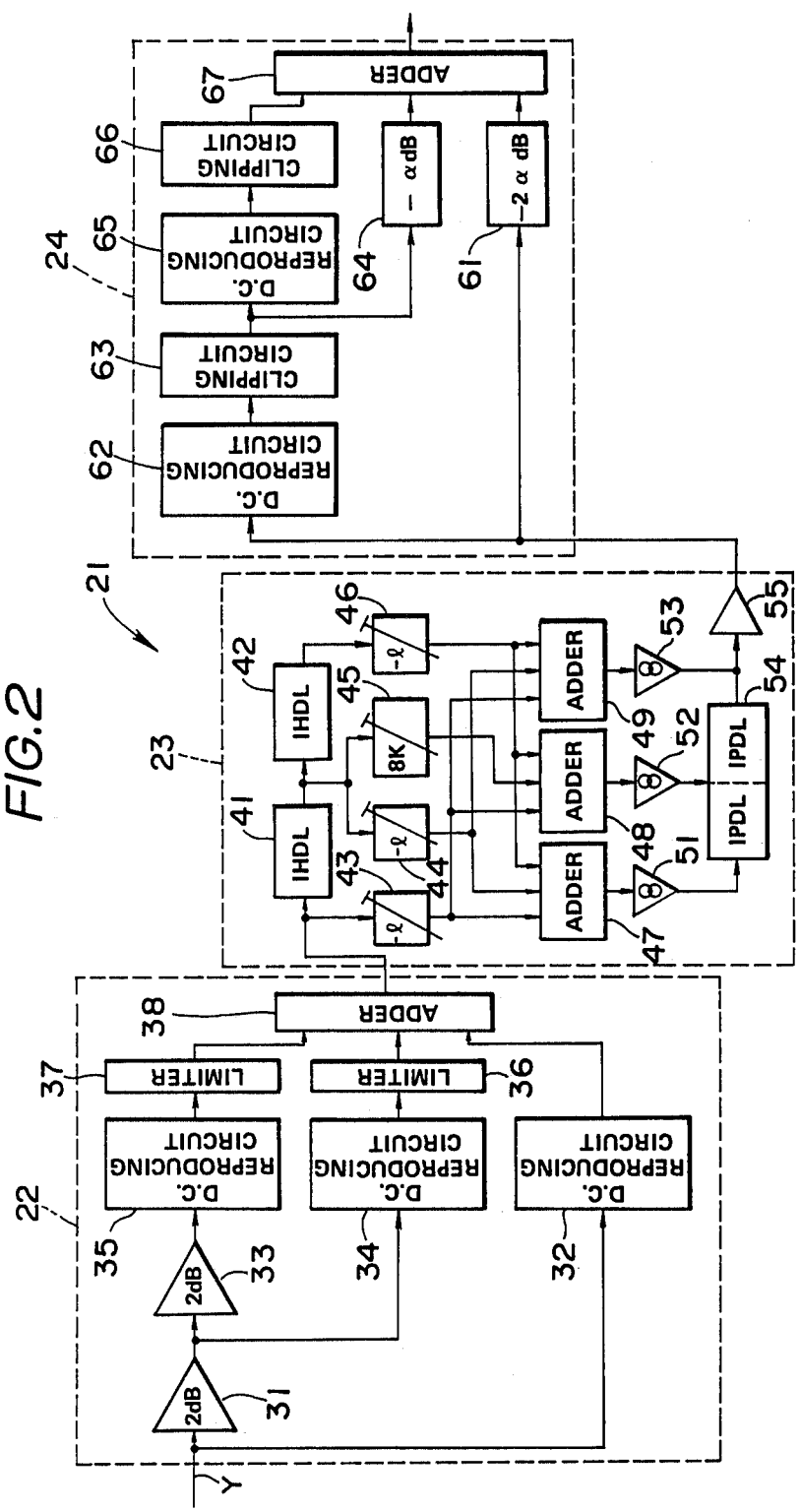

The logarithmic filtering circuit 22 is of such formation as is shown in FIG. 2.

The brightness signal Y (put out of the matrix circuit 17 shown in FIG. 1) is put into the first linear amplifier 31 forming the logarithmic amplifier 22 and is also put into the first direct current reproducing circuit (dynamic clamping circuit) 32. The signal amplified, for example, by 2 dB by this first linear amplifier is put into the second linear amplifier 33 and is also put into the second direct current reproducing circuit 34. Also, the signal amplified, for example, by 2 dB by the second linear amplifier 33 is put into the third direct current reproducing circuit 35. The signals having had the direct current levels shifted by the above mentioned respective direct current reproducing circuits 34 and 35 have respectively the parts below the limiter level Li taken out by the limiters 36 and 37. The outputs of the limiter circuits 36 and 37 and direct current reproducing circuit 32 are added by the adder 38 and, as shown in FIG. 3, an output signal Y log of a logarithmic characteristic is obtained against the input signal.

Figure 3:
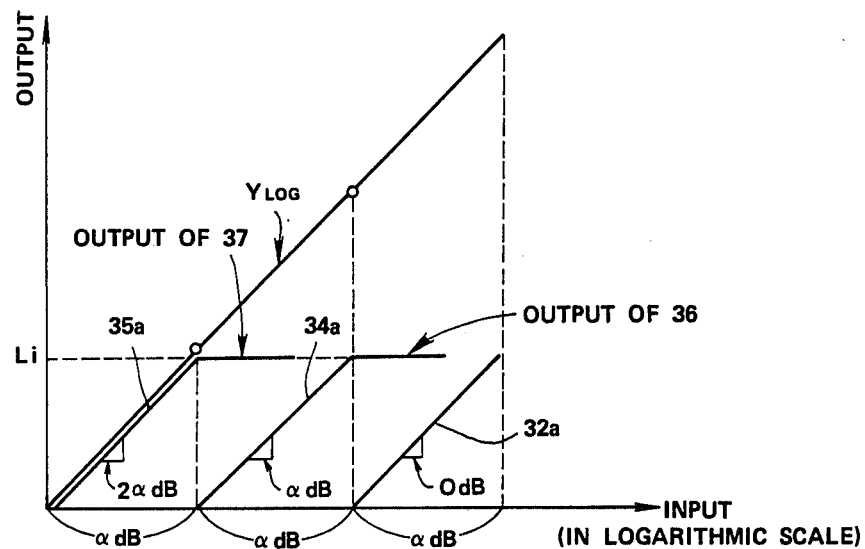

In the above mentioned FIG. 3, in case the signal is put into the adder 38 through the direct current reproducing circuit 32, the output characteristic part of the direct current reproducing circuit 32 is 32a and, after the signals are passed respectively through the first linear amplifier 31 and through the linear amplifiers 31 and 33, the output characteristic parts of the direct current reproducing circuits 34 and 35 are respectively 34a and 35a. The output of the above mentioned second direct current reproducing circuit 34 in the range below the level clipped by the upper limiter level Li is put into the adder 38 side. The input signal on the upper side of the above mentioned limiter level Li is put into the adder 38 (after passing through the direct current reproducing circuit 32) not through the linear amplifiers 31 and 33. In the output of the direct current reproducing circuit 35, the upper limit is limited by the above mentioned limiter level Li. The output signals having passed through the above mentioned limiter circuits 36 and 37 and added by the adder 38 become logarithmic outputs against the input signals.

In the above mentioned logarithmic amplifier 22, a logarithmic characteristic is realized by a broken line approximation such as is shown by FIG. 3. If the number of the linear amplifiers and the number of the direct current reproducing circuits and limiter circuits accompanying them are increased, a more precise logarithmic characteristic can be realized.

The brightness signal logarithmically compressed by the above mentioned logarithmic amplifier 22 is put into a two-dimensional filter 23 in the next step. This two-dimensional filter 23 is formed of delay lines 41 and 42 using CCD's or the like delaying input signals for one horizontal period (mentioned as 1H), coefficient multipliers 43, 44, 45 and 46 multiplying the respective nondelayed, 1H-delayed and 2H-delayed signals, three adders 47, 48 and 49, current source converters 51, 52 and 53 in series respectively with these adders 47, 48 and 54 for two picture elements and an impedance converter 55.

The above mentioned two-dimensional filter 23 concretely realizes a filter characteristic of relatively suppressing the low band side and enhancing the signal component on the high band side. The operating principle of this two-dimensional filter 23 shall be explained in the following.

Figure 4:
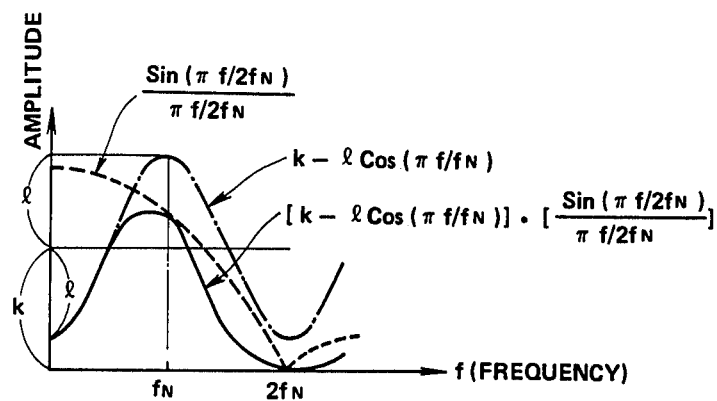

Now, briefly speaking, only the x direction in the picture image is noted (that is, thought in one dimension). Such filtering as is shown in FIG. 4 is carried out.

That is to say, the characteristic function G(f) required to carry out this filtering is represented by the product of two characteristic functions G1(f) and G2(f), that is, $$[K-1 \cos(\pi f/f_N)] \cdot [\sin(\pi f/Z\ f_{NN})/(\pi f/2 f_N)]$$

where f is a spatial frequency, $f_N$ is a Nyquest frequency, k and l are parameters enabling the filter characteristic to be variably set and the above mentioned G2(f), that is, $$\sin(\pi f/2\ f_N) / (\pi f/2\ f_N)$$

is a so-called thinking function.

Figure 5:
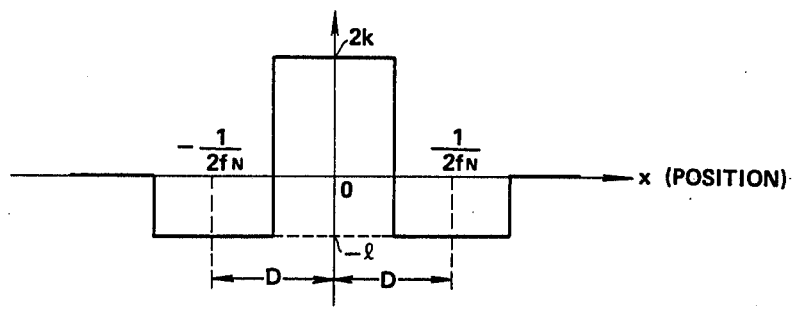

In the coordinate space for obtaining the filter characteristic of the above mentioned characteristic function G(f), the impulse responding (reverse Fourier converting) function h(x) is a negative pulse having a picture element pitch D, a central pulse height of 2K and pulse heights of $-1$ on both sides as shown in FIG. 5. Here, the picture element pitch D is $D = 1/(2f_N)$.

If the convolution h(x)*y(x) of the waveform function h(x) shown in the above mentioned FIG. 5 and the brightness signal y(x) is determined, the filtering of a characteristic such as is indicated by the solid line in FIG. 4 can be made by the frequency folding theory.

Figure 6:
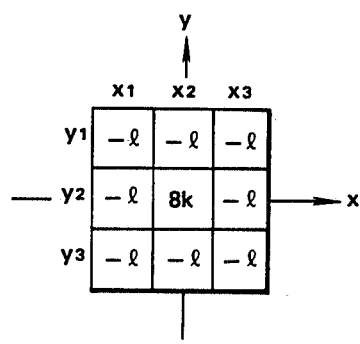

If it is expanded to the two-dimensions, by the overlapping theory, overlapping in the total of four directions of the longitudinal, lateral and two diagonal directions will be made and, as shown in FIG. 6, a coefficient distribution having 8K in the center and $-1$ around it will be made. In the concrete method of making the convolution of this coefficient distribution and the picture image brightness signal, when the brightness signal of the picture element of $(x_2, y_2)$ is put out, the brightness signals of the eight peripheral picture elements $(x_1, y_1)$ to $(x_3, y_3)$ will be simultaneously put out and, by multiplying them by a predetermined coefficient, a total sum may be taken. It is therefore necessary to make the picture elements of $(x_1, y_1)$ to $(x_3, y_3)$ parallel in respect of the time. For example, the brightness signal of the picture element of $(x_2, y_2)$ is required to be delayed by (1H +1 picture element). The concrete circuit realizing it and shown in FIG. 2 shall be explained. The brigtness signal of the picture element of $(x_2, y_2)$ is delayed by 1H through the CCD delay line, is then multiplied by a predetermined coefficient by the coefficient multiplier, is passed through the adder 48, is put into the current source converter 52 and is converted to a current signal by the current source converter 52, is then put into an intermediate tap of the concentrated fixed number type delay line 54 for two picture elements, is delayed by one picture element, is further reconverted to a voltage signal by the characteristic impedance of this delay line and is put out. That is to say, the brightness signal of the picture element $(x_2, y_2)$ is multiplied by a delay of (1H+1 picture element) and a predetermined coefficient. The brightness signals of the other picture elements are also multiplied by a predetermined delay and coefficient in the same manner, are added with an electric current by the adders 47, 48 and 49 and the concentrated fixed number type delay line 54 for two picture elements and are put out as a total sum. The reason here why the signals are converted to current signals by the current source converters 51, 52 and 53 and are added with the current by the concentrated fixed number type delay line 54 is because such concrete circuit as is shown in FIG. 7 is formed, that is to say, by the current signal conversion and current addition, as shown in FIG. 7, the coefficient multipliers 43, 44, 45 and 46, adders 47, 48 and 49 and current source converters 51, 52 and 53 in FIG. 2 can be formed of only three transistors Tr1, Tr2 and Tr3, the delay line 54 may be one and therefore the curcuit can be greatly simplified.

Figure 7:
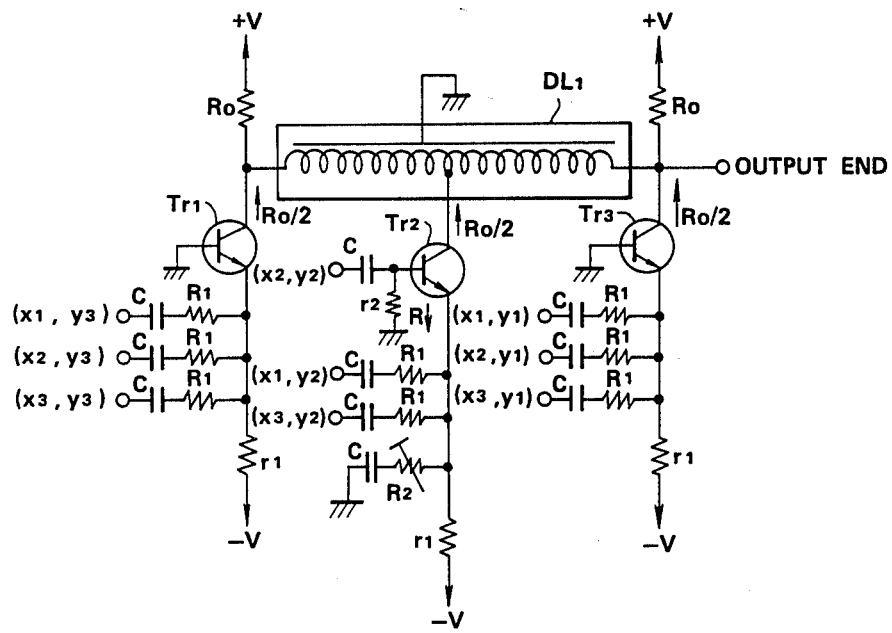

In FIG. 7, the first transistor Tr1 is grounded at the base, has a bias current setting resistance r1 connected to a negative current feeding end $-V$ at the emitter and has brightness singals corresponding to $(x_1, y_3)$, $(x_2, y_3)$ and $(x_3, y_3)$ shown in FIG. 3 applied respectively through coupling condensers C and resistances R1. These respective applied brightness signals are added with the electric current. The above mentioned first transistor Tr1 is connected at the collector to a positive current feeding end $+V$ through a coordinating resistance Ro and is connected to a delay line DL1 of 2H having an intermediate tap.

Against the input impedance (substantially equal to R1) of the respective brightness signals put in through the above mentioned condenser C and resistance R1, the delay line DL1 is set at an impedance ($=$Ro) equal to the coordinating resistance Ro so that the signals can be put out also on the delay line DL1 side without being reflected. Also, the input side impedance R1 and output side impedance Ro/2 are set to be (Ro/2)/R1=1 so that the output signal may be −1 times the predetermined coefficient.

The second transistor Tr2 has a brightness signal corresponding to $(x_2,y_2)$ applied at the base through the condenser C. It is ground at the base through the condenser C. It is ground at the base through a bias setting resistance r2. This transistor Tr2 is connected at the collector to the intermediate tap of the delay line DL and at the emitter to a negative current feeding end −V through a resistance r1, has the brightness signals $(x_1,y_2)$ and $(x_3,y_2)$ applied respectively through the condensers C and resistances R1 and is ground at the emitter through a coefficient setting resistance R2 and direct current rejecting condenser C. The value of this resistance R2 is set so that the emitter side synthesized impedance R may be $8K=(Ro/2)/R$ to the collector side impedance Ro/2.

The third transistor Tr3 is of the same formation as of the first transistor Tr1 and its collector is an output end.

In the two-dimensional filter 23 shown in the above mentioned FIG. 2, if the values of the coefficient multipliers 43, 44 and 46 are made variable, the value of 1 in the filter characteristic can be made variable and, if the value of the coefficient multiplier 45 is made variable, the value of k can be made variable. For example, if the value of 1 is made variable to be of the characteristic shown in FIG. 8(a), a bypass filter can be made and a low frequency component such as the illumination unevenness can be suppressed. If it is made to be of the characteristic shown in FIG. 8(b), the high frequency component can be enhanced also from the low band side and the outline and structure can be enhanced. FIG. 8 shows the amplitude as standardized.

The brightness signal properly filtered by the above mentioned two-dimensional filter 23 is put into an attenuator 61 attenuating the signal, for example, by $-2\alpha dB$ and is put into an attenuator 64, for example, of $-\alpha dB$ through a series circuit of a direct current reproducing circuit 62 and a clipping circuit 63 clipping below a predetermined level. The brightness signal clipped by the above mentioned clipping circuit 63 is passed through a direct current reproducing circuit and a clipping circuit 66 in series, is added by an adder 67 together with the signals having passed respectively through the above mentioned attenuators 61 and 64 and is put out. The signal put in by the above mentioned exponential amplifier 24 is converted to a signal output of an exponential characteristic by such broken line approximation as is shown in FIG. 9.

Figure 9:
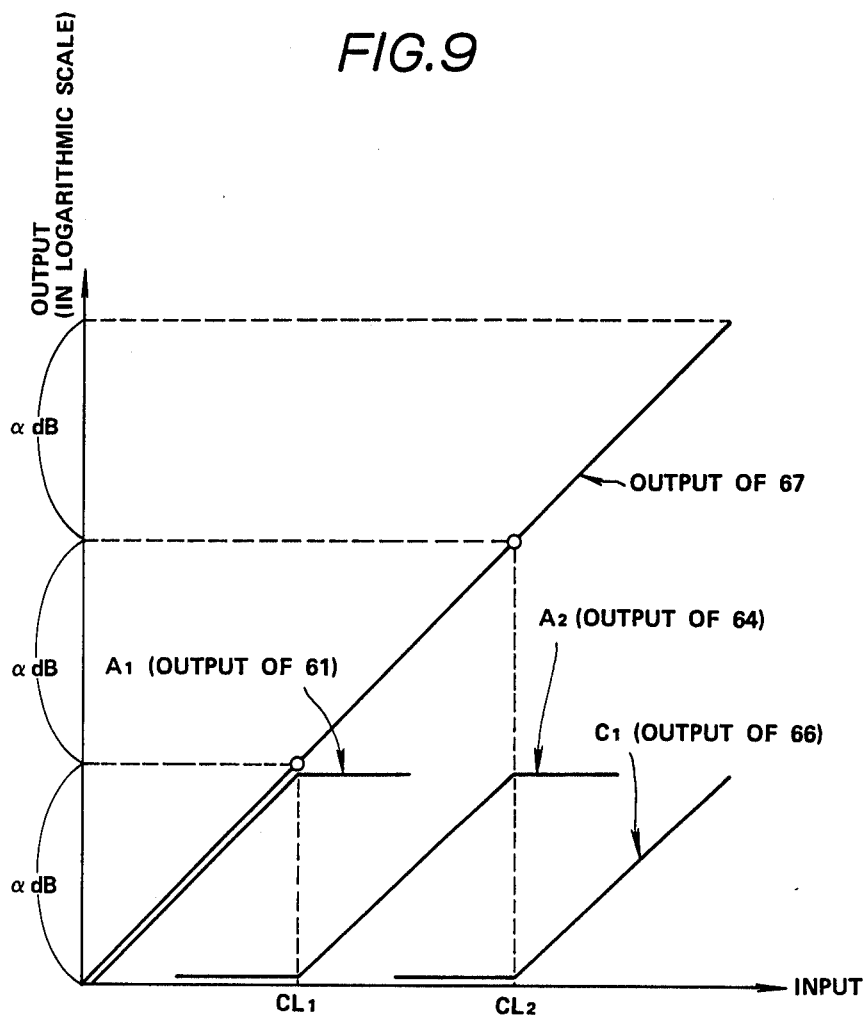

That is to say, the signal put into the exponential amplifier 24 is attenuated by $-2\alpha dB$ by the attenuator 61, is made to be of the waveform shown by $A_1$ in FIG. 9 and is put into the adder 67. Also, the signal having had the level shifted by the direct current reproducing circuit 62 and clipped on the level CL1 by the clipping circuit 63 is passed through the attenuator 64 and is made to be of the characteristic shown by $A_2$ in FIG. 9 and is put into the adder 67. The signal clipped by this clipping circuit 63 has the level shifted by the direct current reproducing circuit 65 in the same manner, is clipped on the level CL2 by the clipping circuit 66, is made to be of the output characteristic shown by $C_1$ in FIG. 9 and is put into the adder 67. These $A_1$, $A_2$ and $C_1$ are added by the adder 67 and are converted to be of the exponential characteristic shown in FIG. 9.

If the number of the clipping circuits and the number of the accompanying attenuators are increased, the above mentioned exponential amplifier 24 can be more precisely approximated.

Figure 10:
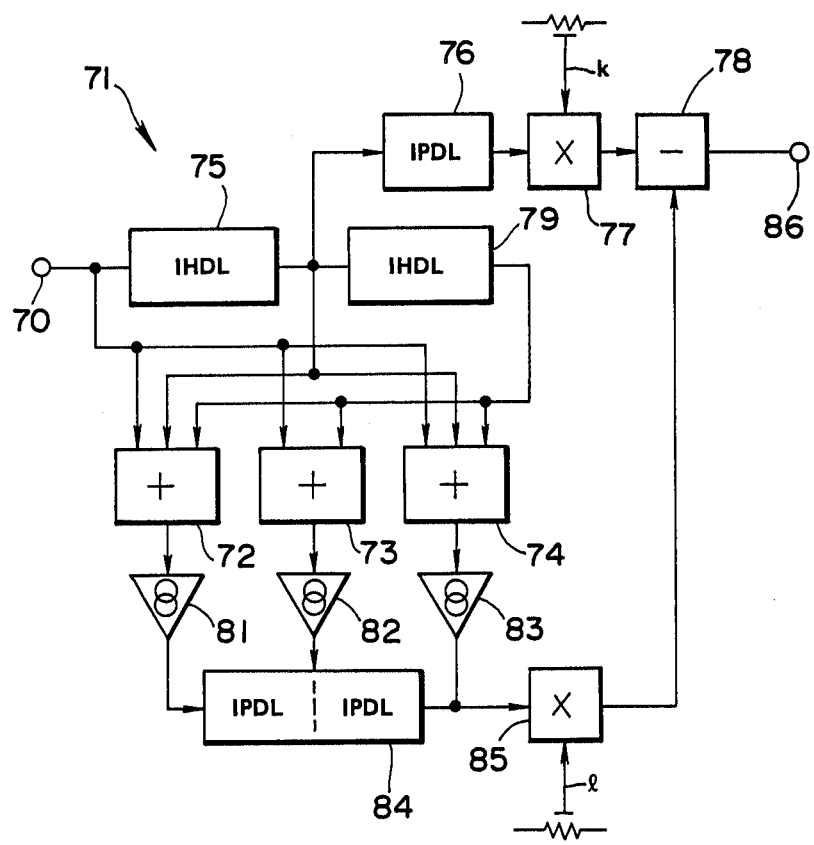
FIG. 10 is a block diagram showing another embodiment of the two-dimensional filter.

FIG. 10 shows the formation of a two-dimensional filter in the second embodiment of the present invention.

In this two-dimensional filter 71, the input signal fed to the input end 70 is put into three of the first, second and third adders 72, 73 and 74 and is put into the first and third adders 72 ad 74 through a 1H-delay line 75. The output of this 1H-delay line 75 is put into a multiplier 77 through a concentrated fixed number type delay line 76 for one picture element, is multiplied by a coefficient K, is put into a subtractor 78 and is put into the three adders 72, 73 and 74 through a 1H-delay line 79. The signals added by the respective adders 72, 73 and 74 are passed respectively through current source converters 81, 82 and 83 and are applied respectively on the input end, intermediate tap and output end of a delay line 84 making a delay for two picture elements. The output of this delay line 84 is put into a multiplier 85, is multiplied by the coefficient 1, is then put into the above mentioned subtractor 78, is subtracted from the output of the multiplier 77 and is put out of the output end 86.

According to this second embodiment, the values of the parameters k and l for filtering can be manually set by the multipliers 77 and 85 so as to be variable and the filter characteristic can be freely set.

Figure 11:
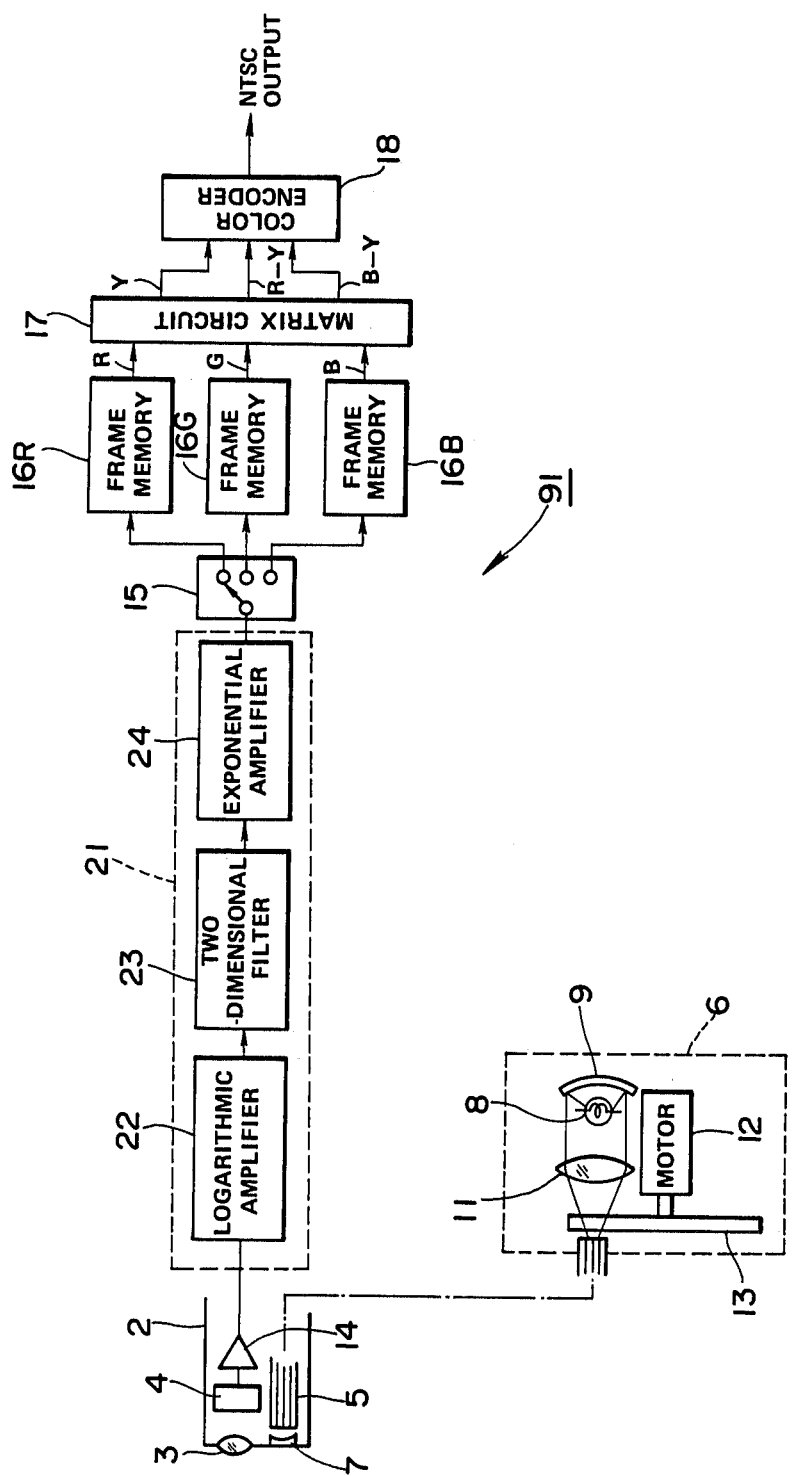
FIG. 11 is a formation view showing another embodiment of the electronscope in the present invention.

FIG. 11 shows a formation example of an electronscope of a formation different from that in FIG. 1.

In this electronscope 91, the logarithmic filtering circuit 21 is interposed between the preamplifier 14 and multiplexer 15.

The operation of the logarithmic filtering circuit 21 in this electronscope 91 is the same as is shown in FIG. 1.

A means of displaying on the displayed picture surface the values of the parameters k and l defining the filter characteristic in the above mentioned logarithmic filtering circuit 21 may be provided so as to be able to be ultilized as data in diagnosing. For example, the values of k and l at which a picture image is influenced little by the illumination unevenness and is easy to diagnose can be known. Also, the degree of enhancing the high band side to clear the outline can be known.

The two-dimensional filter 23 in the above mentioned logarithmic filtering circuit 21 is not limited to the above described one. For example, by a differential operation, the high band may be enhanced to clear the outline. In such case, by simultaneously using the filter characteristic of suppressing the low band side, filtering may be made to prevent the latitude from being reduced by the illumination unevenness or the like.

In the above described embodiment, the illumination and image pickup of the face successive system are made. However, the present invention is not limited to this system but can be applied in the same manner to a color image pickup system using a solid state image pickup element for color video images under a white illumination.

The present invention can be applied not only to color image signals but also to monochromatic image signals.

The present invention is not limited to be used for the electronscope.

Also, it can be easily presumed that the present invention is not limited to analogously filtering but can be formed of digital circuits though disadvantageous in respect of the quantum eror and circuit scale because a non-lenear process is interposed.

As described above, according to the first embodiment, in the two-dimensional filter, the low band side is suppressed and the high band side is relatively enhanced in the logarithmically compressed image signal in filtering. As the image signal having passed through this two-dimensional filter is returned to the original image signal through the exponential characteristic converting means, the latitude can be prevented from being reduced by the illumination unevenness and a clear picture image can be obtained by enhancing the structure. Therefore, a clear picture image which does not become too dark even in the far part and is easy to diagnose can be obtained.

Figure 12:
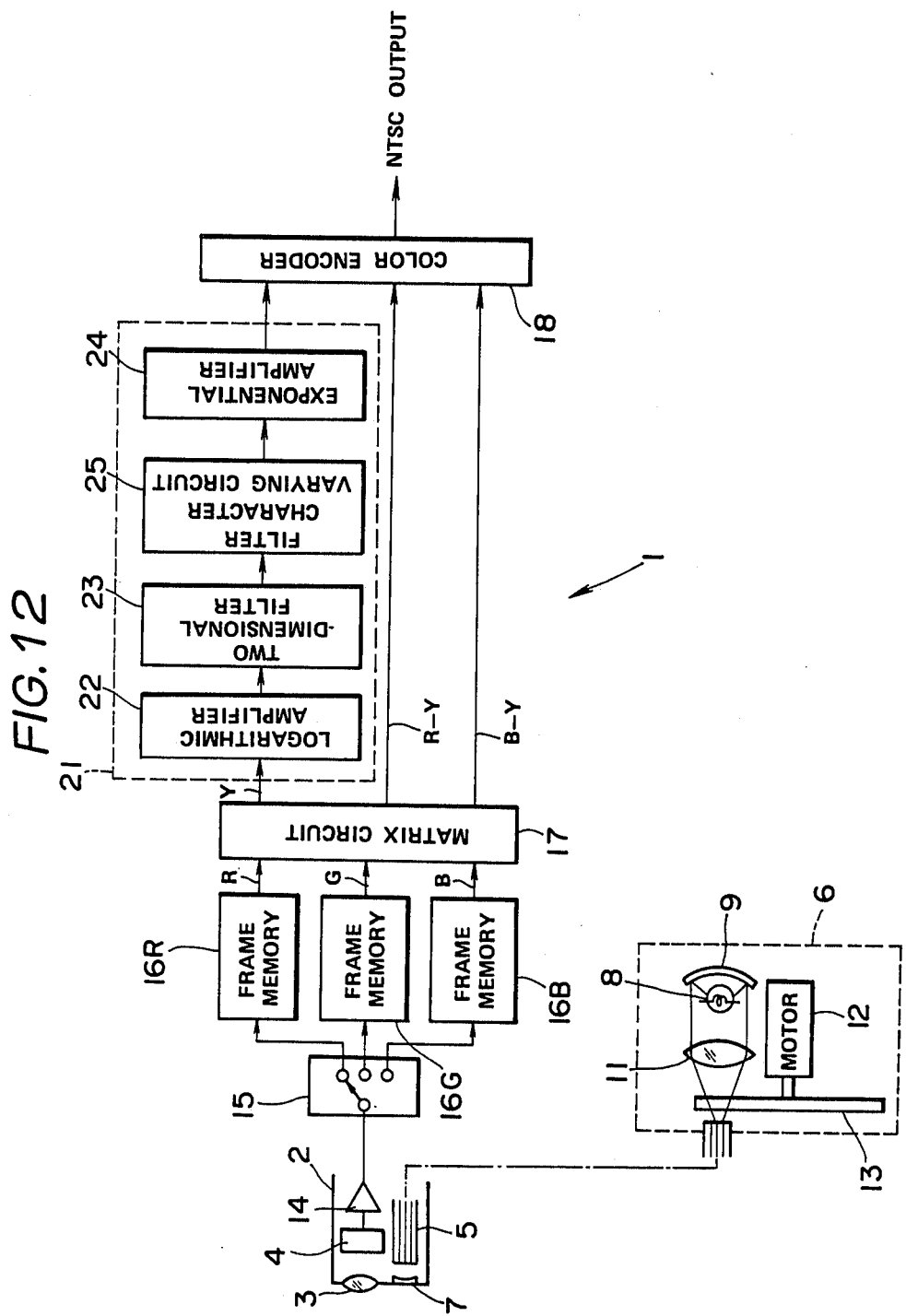

The second embodiment shall be explained in the following with reference to FIG. 12 and others following it. The second embodiment shown in FIG. 12. is different only in the formation of the logarithmic filtering circuit 21 from the first embodiment in FIG. 1 but is the same as in FIG. 1 in the other formation. The logarithmic filtering circuit 21 is formed of a logarithmic amplifier 22 logarithmically compressing an input brightness signal Y, a two-dimensional filter 23 showing a bypass filtering characteristic of relatively suppressing the low band side and enhancing the high band side of this logarithmically compressed brightness signal Y, a filter characteristic varying circuit 25 wherein the signal having passed through this two-dimensional filter 23 is put in and this filter characteristic is made variable and an exponential amplifier 24 wherein the output signal of this filter characteristic varying circuit is put in and an exponential function is put out.

The same as in the case of FIG. 1, the brightness output log $Y(x',Y')$ logarithmically compressed by the logarithmic amplifier 22 is represented by log $Y(x',y')$ = log $F(x',y')$ = log $G(x',y')$. As the intensity distribution by the illumination unevenness is usually of a low frequency, by passing the signal through the two-dimensional filter 23 passing it through the high band side, the element jog $F(x',y')$ by the illumination unevenness can be substantially eliminated and only the brightness signal represented by log $G(x',y')$ can be taken out. This signal is passed through the filter characteristic varying circuit 25 in the next step wherein the gain on the low band side and the gain on the high band side can be respectively independently and variably set. In this case, in the filter characteristic varying circuit 25, if the gain on the low band side is suppressed, the influence of the illumination unevenness caused on the low band side can be eliminated or reduced. If the high band side is enhanced, the outline and structure in the frequency band on the high band side can be enhanced. A noise suppressing circuit 26 and $\gamma$-correcting circuit 27 (See FIG. 13) are provided within this filter characteristic varying circuit 25 so that the noise in the case that S/N is small and the noise increased particularly by the high band enhancement may be suppressed not to be conspicuous to the sight. The signal filtered through this filter characteristic varying circuit 25 has the exponent converted by the exponential amplifier 26 and is returned to be of the original characteristic.

Thus, in the logarithmic filtering circuit 21, relatively the low band side is suppressed and the high band side is enhanced to eliminate the illumination unevenness and to enhance the outline and structure. The noise in the enhanced frequency band will be also enhanced, therefore the noise of a small amplitude in the original signal of a small amplitude will be conspicuous to the sight as a random noise and the S/N will deteriorate. Therefore, the part considered to be the noise of the small amplitude is clipped so that the gain on the small amplitude side may become small to suppress the noise and the picture image may be processed to obtain a displayed picture surface easy to diagnose in the sight.

Figure 13:
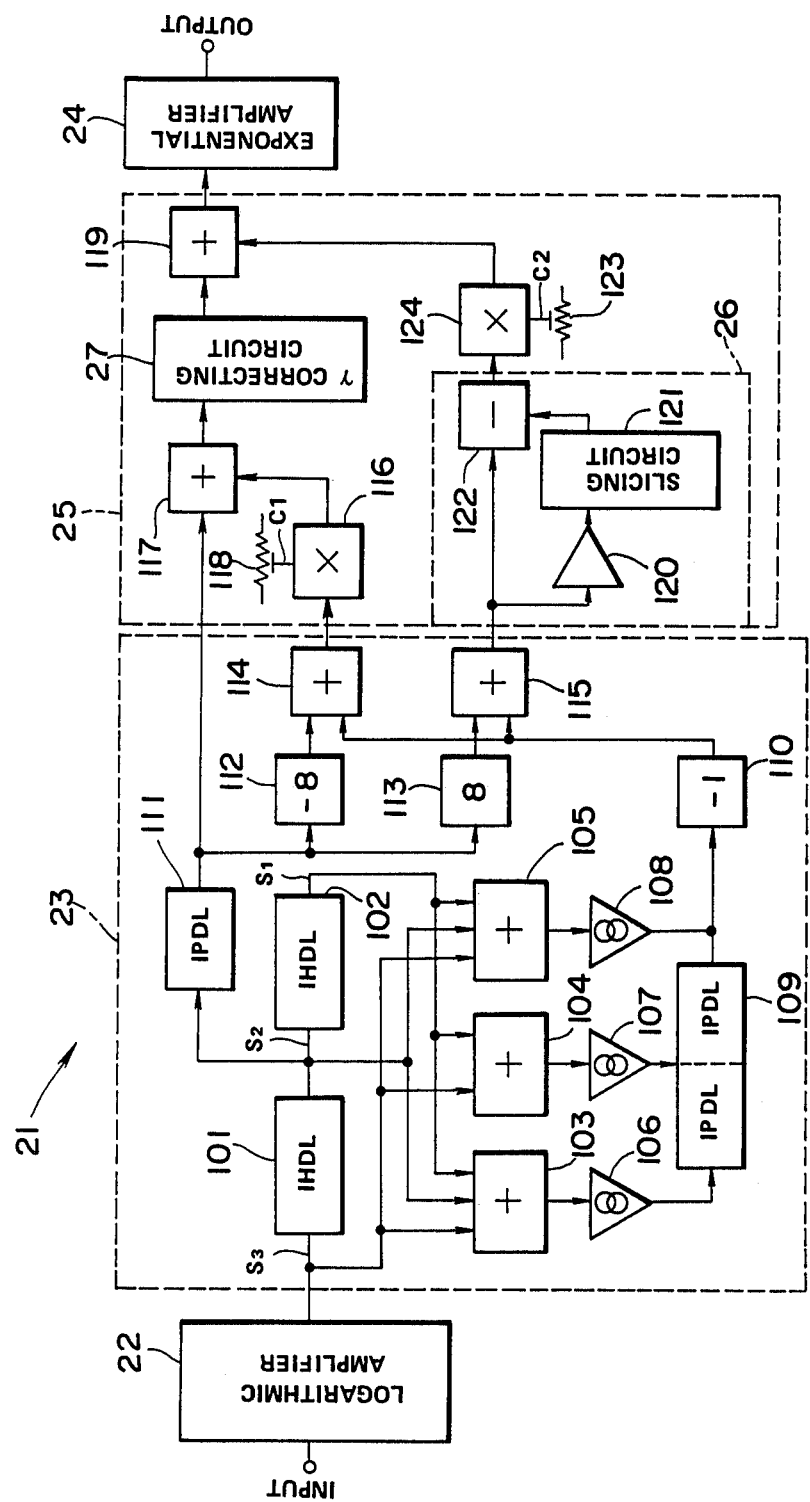

Now, a concrete formation example of the above mentioned logarithmic filtering circuit 21 is shown in FIG. 13.

The brightness signal logarithmically compressed by the logarithmic amplifier 22 is put into the two-dimensional filter 23 in the next step. This two-dimensional filter 23 is formed of delay lines 101 and 102 using CCD's delaying the input signal by 1 horizontal period (mentioned as 1H), three adders 103, 104 and 105 adding respectively non-delayed, 1H-delayed and 2H-delayed signals, current source converters 106, 107 and 108 in series respectively with these adders 103, 104 and 105, a two-picture element concentrated coefficient type delay line 109, a coefficient multiplier 110 multiplying the output of this delay line 109 by a coefficient, for example, of $-1$, a delay line 111 delaying by one picture element the signal having passed through the above mentioned 1H-delay line, coefficient multipliers 112 and 113 making outputs by multiplying the output signal of this delay line 111 respectively by the coefficients, for example, of $-8$ and 8 and adders 114 and 115 respectively adding and putting out the output signals of the respective coefficient multipliers 112 and 113 and the output signal of the above mentioned coefficient multiplier 110.

As shown in FIG. 14, in the above mentioned two-dimensional filter 23, such impulse response FIR (finite impulse response) as is shown in FIG. 15 is made in four directions of the horizontal direction, vertical direction, oblique direction at an angle of 45 degrees and oblique direction at an angle of 135 degrees on signals S $(x_i,y_i)$ corresponding to the respective picture element positions $(x_i,y_i)$ (where i=1, 2 and 3). When this impulse response shown in FIG. 15 is made, the filter characteristic indicated by a in FIG. 16, that is, the filter characteristic of $$[1 - \cos(\pi f/2\ f_n) / (\pi f/2\ f_n)]$$

will be made in the spatial frequency band. (In this embodiment, in order to make the filter characteristic variable, the level shifting signal and the signals indicated by a and b in FIG. 16 are put out of the two-dimensional filter 23.)

The impulse response shown in FIG. 15 is of a negative pulse in which the pulse width has the picture element pitch D and the pulse heights are 2 in the middle and $-1$ on both sides. This picture element pitch D is $D = 1/(2f_N)$ where $f_N$ is a Nyquest frequency.

In case the impulse response in FIG. 15 is made in the respective arranging directions of four picture elements, the brightness signal will be put in in the horizontal direction along the scanning line. Therefore, as shown in FIG. 13, the delay lines 101, 102 and 109 are used.

For example, the signal $S_1$ put in along the first horizontal line is delayed by the 2H period through the delay lines 101 and 102, is thereby synchronized with the signal $S_2$ of the second horizontal line delayed by the 1H period through the delay line 101 and is further synchronized with the signal $S_3$ of the third horizontal line put in with no delay.

The above mentioned signal $S_1$ is passed through the respective adders 103, 104 and 105 and series current source converters 106, 107 and 108, is delayed by two picture elements, delayed by one picture element and not delayed to have the signals of $(x_1,y_1)$, $(x_2,y_1)$ and $(x_3,y_1)$ along the first horizontal line added and is put into the $-1$ coefficient multiplier 110. In the same manner, also the signal $S_2$ having passed through the delay line 101 is passed through the respective adders 103 and 105 and series current source converters 106 and 108, is further delayed by two picture elements and not delayed in the delay line 109 to thereby have the signals of $(x_1,y_2)$ and $(x_3,y_2)$ added and is put into the coefficient multiplier 110. In the same manner, the signal $S_3$ along the third horizontal line is passed through the adders 103, 104 and 105 to have the signals of $(x_1,y_3)$, $(x_2,y_3)$ and $(x_3,y_3)$ added and is put into the coefficient multiplier 110. That is to say, the other signals than in the picture element position $(x_2,y_2)$ in the center (of FIG. 14) are put into the $-1$ coefficient multiplier 110. The signal in the picture element position $(x_2,y_2)$ in the above mentioned center is passed through the delay line by one picture element 111 (to be synchronized with the other signal put into the $-1$ coefficient multiplier), is put into the coefficient multipliers 112 and 113 and the outputs of these respective coefficient multipliers are put into the adders 114 and 115 to have the signal having passed through the $-1$ coefficient multiplier 110 added.

The signal output put out of the above mentioned adder 114 is indicated by b in FIG. 16. The signal output of the adder 115 is indicated by a in FIG. 16. The signal output from the delay line 111 is indicated by c in FIG. 16. In the filter characteristics indicated by a and c in FIG. 16, the gain on the low band side is small, the passing gain on the high band side is large and the illumination unevenness on the low band side can be eliminated.

The output signal of the above mentioned adder 114 is put into the adder 117 through the multiplier 116 forming the filter characteristic varying circuit 25 and has the brightness signal having passed through the delay line 111 added.

In the above mentioned multiplier 116, by the variable resistor 118, the amplitude of the characteristic indicated by b in FIG. 16 can be variably set by the multiplying coefficient $C_1$. By making this coefficient $C_1$ variable, the amplitude on the high band side can be set to be variable (independently of the low band side) and the outline enhancement and structure enhancement in the high frequency band can be made variable.

The enhanced signal added in the above mentioned adder is $\gamma$-corrected in the $\gamma$-correcting circuit 27, has the signal on the side passed through the noise suppressing circuit 26 added in the adder 119 and is put out.

Now, the above mentioned noise suppressing circuit 26 comprises a twice-amplifier 120 twice amplifying the signal having passed through the adder 115, a slicing circuit 121 slicing the output of this amplifier 120 on the level L considered to be the noise level and taking out this part and a subtractor 122 subtracting the output signal of this slicing circuit 121 from the signal having passed through the above mentioned adder 115.

Figure 17:
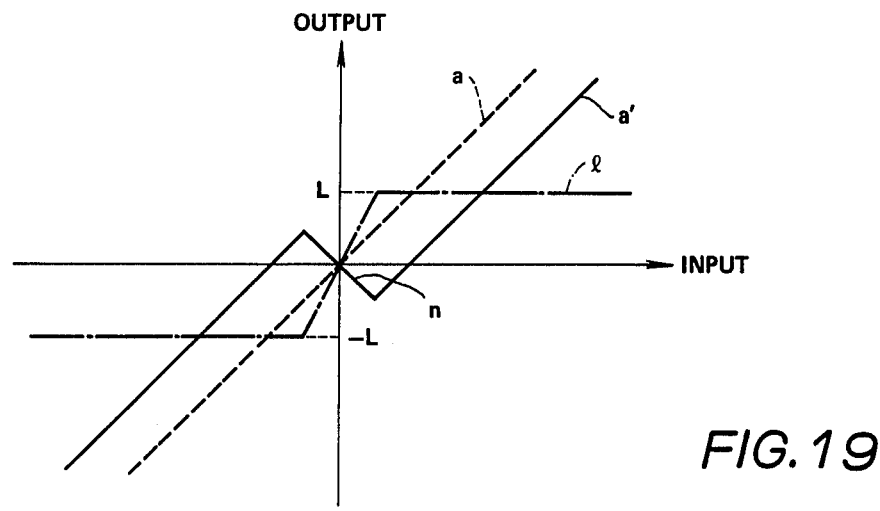

When the signal part put into the above mentioned noise suppressing circuit 26 is indicated by the dotted line a in FIG. 17, the part amplified by the twice-amplifier 120 and sliced by the slicing circuit 121 will be indicated by the one-point chain line 1 in FIG. 17. If this sliced part is subtracted, the signal of the characteristic indicated by the solid line a' in FIG. 17 and having had the noise suppressed can be made. As the characteristic indicated by the solid line a' and having had the noise suppressed indicates a gradient of $-1$ in the noise corresponding band (indicated by n), the signal in this band will be erased or sufficiently suppressed when added by the adder 55.

The signal having passed through the above mentioned noise suppressing circuit 26 is passed through the multiplier 124 capable of variably setting the multiplied coefficient $C_2$ by the variable resistor 123 and is then added in the adder 119.

Figure 18:
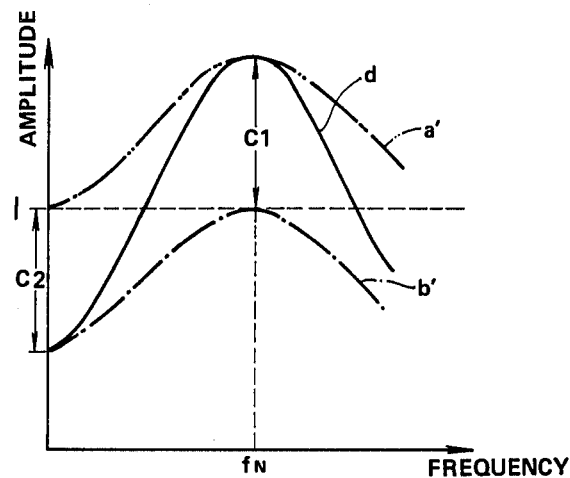

The signal added by the adder 119 is indicated by the solid line d in FIG. 18.

That is to say, the signal b' having passed through the adder 114 and multiplier 116 and the signal a' having passed through the adder 115, noise suppressing circuit 26 and multiplier 124 are added to be of the filter characteristic indicated by the solid line d. In this case, as the signal having passed through the delay line 111 is also added, the level will be shifted by the amplitude 1.

In FIG. 18, the height $C_1$ from the amplitude level 1 of the ridge part in which the Nyguest frequency $f_N$ is maximum can be adjusted by the multiplier 118. The drop (suppressed amount) $C_2$ from the amplitude level 1 in the frequency 0 can be variably adjusted by the multiplier 124.

Therefore, by varying the value of $C_1$, the enhancement of the high band side, that is, the size of the enhancement of the outline and structure can be variably set. Also, by varying the value of $C_2$, the suppressed degree of the low band side can be variably set, that is to say, the outline or the like so dark due to the illumination unevenness as not to be seen can be made bright and the gain of the part too bright due to the illumination unevenness can be reduced to eliminate or reduce the influence of the illumination unevenness.

When the high band side is enhanced, the noise level on the high band side will be so high that particularly, in the signal of a small amplitude, this noise will be conspicuous to the sight. However, such noise can be eliminated or suppressed by the noise suppressing circuit 26.

The enhanced signal of the high band side added by the adder 117 is $\gamma$-corrected by the $\gamma$-correcting circuit 27 before the other enhanced signal is added to it by the adder 119. Thus, by applying the human sight characteristic that, "in the signal of a low brightness, the random noise is conspicuous but, in the signal of a high brightness, even if the noises of the same amplitude are overlapped, they will not be conspicuous", an enhanced signal is made of a video image signal before being $\gamma$-corrected, is passed through the $\gamma$-correcting circuit 27 and is then added. That is to say, the signal is $\gamma$-corrected before it is returned to be of an ordinary linear input-output characteristic by the exponential amplifier 24 so that the enhanced signal on the displayed picture surface after the exponential amplifier 24 may be of a reverse $\gamma$-characteristic. That is to say, the gain in which the amplitude of the brightness signal level is small is suppressed so that the noise in the signal in which the N/S is small may not be conspicuous to the sight.

According to this embodiment, the gain amount for the high band side can be made variable by the value of $C_1$ by the variable resistor 118, the suppressed amount for the low band side can be made independently manually variable by the value of $C_2$ by the variable resistor 123, therefore the outline and structure of the picture image can be enhanced and the illumination unevenness can be effectively eliminated. As the brightness signal between the logarithmic amplifier 22 and exponential amplifier 24 is $\gamma$-corrected, the $\gamma$-correction and the reduction of the unsightly noise can be simultaneously made.

Also, by the noise suppressing circuit 26, the enhancement of the outline and structure and the suppression of the noise can be simultaneously made.

Figure 19:
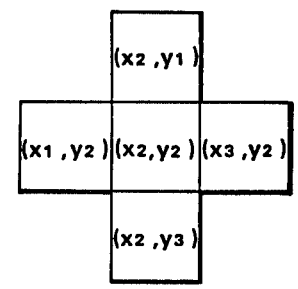
FIG. 19 is an explanatory view showing another picture element arrangement.

In the above mentioned embodiment, the image is processed by the impulse response in four directions but the present invention is not limited to it. For example, as shown in FIG. 19, the processing by the response as shown in FIG. 15 may be made in two horizontal and vertical directions. In such case, the formation of the two-dimensional filter part in FIG. 13 can be made simpler.

In the present invention, the two-dimensional filter characteristic may be formed by filtering by a differential operation or the like.

The present invention can be applied to a color image signal and its brightness signal and naturally also to a monochromatic image signal.

Also, the present invention can be applied in the same manner to the brightness signal in the case of not only an endoscope illuminating and imaging in the color face order but also a color image pickup means illuminating with a white illuminating light and using a solid state image pickup element provided with such color filter as is mosaic-like on the front surface.

Further, the present invention can be extensively applied not only to an endoscope but also to the case of displaying image signals on a color or monochromatic picture surface.

As described above, according to the second embodiment, as the gain on the high band side and the gain on the low band side are made respectively independently variable, the elimination of the illumination unevenness produced on the low band side and the enhancement of the outline and structure belonging to the high band side can be effectively made and a picture image easy to diagnose can be obtained.

It is apparent that, in the present invention, working modes different in a wide extent can be formed on the basis of this invention without deviating from the spirit and scope of the invention. This invention is not restricted by such specific working modes except being limited by the appended claims.

What is claimed is:

1. An image signal correcting circuit characterized by an image signal correcting means comprising:
   a light guide;
   a light source means for providing an illumination light through the light guide for an observed object;
   a logarithmic compressing means for logarithmically compressing an image signal;
   a two-dimensional filter means for relatively suppressing a low band component to eliminate an illumination unevenness caused by the illumination light and enhancing a high band component of said logarithmically compressed signal; and
   an exponential converting means for converting the image signal, having passed through said two-dimensional filter means, to be of an exponential characteristic.

2. An image signal correcting circuit according to claim 1 wherein said two-dimensional filter means has a filter characteristic variable means which can variably set a signal gain for the high band component and a signal gain for the low band component respectively independently.

3. An image signal correcting circuit according to claim 1 wherein said two-dimensional filter means comprises a delaying means consisting of two 1H-delay parts each delaying by 1H a picture signal from said logarithmic compressing means, a coefficient multiplying means for multiplying through a coefficient multiplier respective non-delayed, 1H-delayed and 2H-delayed signals from said delaying means by a coefficient, an adding means consisting of three adders for adding the non-delayed, 1H-delayed and 2H-delayed signals having passed through said coefficient multiplier, a current converting means for converting signals, having passed through said adders, to current signals, a current adding means consisting of a delay part for two picture elements for current-adding signals from said current converting means and an impedance converting means for putting out said current-added signals.

4. An image signal correcting circuit according to claim 1 wherein said two-dimensional filter means comprises a first delaying means consisting of two 1H-delay lines each delaying by 1H the image signal from said logarithmic compressing means, an adding means for adding through adders respective non-delayed, 1H-delayed and 2H-delayed signals from said first delaying means, a second delaying means for delaying by one picture element the 1H-delayed signal from said first delaying means, a first coefficient multiplying means for multiplying by a coefficient the signal from said second delaying means, a current converting means for converting to current signals the signals having passed through said adders, a current adding means consisting of a delay line for two picture elements for current-adding the current signals from the current converting means, a second coefficient multiplying means for multiplying said current-added signals by a coefficient and a subtracting means for subtracting from the signal, from said first coefficient multiplying means, the signals from said second multiplying means.

5. An image signal correcting circuit according to claim 2 wherein said filter characteristic variable means comprises a first gain variable means for making variable the signal gain for the high band component, a $\gamma$-correcting means for $\gamma$-correcting the signal from said first variable means, a second gain variable means for making variable the signal gain for the low band component said second gain variable means including a noise suppressing means for suppressing noises in said logarithmically compressed signal and an adding means for obtaining an added output of the signal from said $\gamma$-correcting means and a signal provided from the noise suppressing means.

6. An image signal correcting circuit according to claim 1 wherein said image signal is a brightness signal in an electronic endoscope.

7. An image signal correcting circuit according to claim 1 wherein said image signal is provided by a solid state image pickup element in an electronic endoscope.

* * * * *